United States Patent
Lin

[11] Patent Number: 5,423,817
[45] Date of Patent: Jun. 13, 1995

[54] INTERVERTEBRAL FUSING DEVICE

[76] Inventor: Chih-I Lin, 513 S. Golden Pardos Dr., Diamond Bar, Calif. 10765

[21] Appl. No.: 348,954

[22] Filed: Nov. 25, 1994

Related U.S. Application Data

[63] Continuation of Ser. No. 98,858, Jul. 29, 1993, abandoned.

[51] Int. Cl.$^6$ .............................................. A61B 17/70
[52] U.S. Cl. ........................................ 606/61; 623/17
[58] Field of Search ...................... 606/61, 72; 623/16, 623/17; 267/166, 169, 178, 179, 180; 411/389, 392, 395, 397, 424

[56] References Cited

U.S. PATENT DOCUMENTS

| | | | |
|---|---|---|---|
| 843,827 | 2/1907 | Knudsen | 267/180 |
| 3,068,666 | 12/1962 | Sabadash | 267/180 |
| 4,501,269 | 2/1985 | Bagby | 606/61 |
| 4,961,740 | 10/1990 | Ray et al. | 606/61 |
| 5,015,247 | 5/1991 | Michelson | 606/72 |
| 5,026,373 | 6/1991 | Ray et al. | 606/61 |

FOREIGN PATENT DOCUMENTS

91/06266  5/1991  WIPO .................................. 623/17

Primary Examiner—Tamara L. Graysay
Attorney, Agent, or Firm—Bacon & Thomas

[57] ABSTRACT

An intervertebral fusing device having a spring body portion interconnecting a first spiral ring mount and a second spiral ring mount. Each spiral ring mount having a spiralling projection on the outer surface. The spring body portion is defined by a plurality of spiral loops. The plurality of spiral loops and spiralling projection of the spiral ring mounts have a constant pitch. A mount cover and a head member are threaded into an internally threaded portion of a respective spiral ring mount thereby forming a chamber in which bone grafts affinitive to the cells and tissues of a vertebra may be housed. The spring body portion is similar in elasticity to the vertebra.

3 Claims, 4 Drawing Sheets

INTERVERTEBRAL FUSING DEVICE

This application is a continuation of application Ser. No. 08/098,858, filed Jul. 29, 1993, now abandoned.

FIELD OF THE INVENTION

The present invention relates generally to a spinal orthopedic device, and more particularly to an intervertebral fusing device.

BACKGROUND OF THE INVENTION

The prior art intervertebral fusing device is made up of a hollow cylindrical body provided therein with an empty space in which bone grafts are contained, and with a perforated wall through which the bone grafts make contact with the vertebrae. A fusion system made by SPINTECH Corp. of the United States is a typical example of such a prior art device as referred to above. The afore-mentioned fusion system is an improved product, which was developed on the basis of the inventive concepts disclosed respectively in U.S. Pat. Nos. 4,501,269 and 5,015,247. The cylindrical body of the prior art device is made of a material having a rigidity, which is about 5–10 times greater than that of the human vertebrae. As a result, the implanted cylindrical body of the prior art device is forced to bear almost entirely the stress exerting on the vertebra under treatment, thereby bringing about a poor contact between the vertebra and the bone grafts contained in the cylindrical body. The healing effect of the prior art device is therefore adversely affected. Moreover, the prior art device described above is further defective in design in that it is deficient in differentials in rigidity.

SUMMARY OF THE INVENTION

It is therefore the primary objective of the present invention to provide an intervertebral fusing device with a spiral elastic body, which serves as a main body of the intervertebral fusing device and is capable of making an extremely small movement, or a micromotion, It is another objective of the present invention to provide an intervertebral fusing device with a spiral elastic body, which serves as a main body of the intervertebral fusing device and has a predetermined associated elasticity.

It is still another objective of the present invention to provide an intervertebral fusing device, which is made up of a spiral elastic body, a spiral head member, and bone grafts affinitive to cells and tissues of the vertebrae under treatment.

In keeping with the principle of the present invention, the foregoing objectives of the present invention are accomplished by an intervertebral fusing device which comprises a spiral elastic body as a main body thereof. The elasticity of the spiral elastic body can be adjusted as desired by altering the roughness and the interval of the coiled portions making up the spiral elastic body, in addition to the quality of the material of which the spiral elastic body is made. In other words, the spiral elastic body of the present invention can be so made as to be similar in elasticity to the vertebrae intended to be treated. Therefore, the stress exerting on the vertebra to be fused can be borne jointly by the spiral elastic body and the vertebrae. In addition, there is an excellent contact between the vertebrae and the bone grafts contained in the device of the present invention, thanks to the spiral elastic body of an appropriate elasticity. With the implantation of the device of the present invention, the healing process of the deformed vertebra under treatment can take place at a relatively fast pace.

The foregoing objectives, structures and functions of the present invention can be more readily understood upon a thoughtful deliberation of the following detailed description of the present invention in conjunction with the accompanying drawings.

BRIEF DESCRIPTION OF THE DRAWINGS

FIG. 2b is a, schematic view showing a spiral head member and a spiral head hole of the implanted device as shown in FIG. 2a.

FIG. 3b is a schematic view showing a spiral head member and a spiral head hole of the implanted device as shown in FIG. 3a.

DETAILED DESCRIPTION OF THE INVENTION

Figure 1:
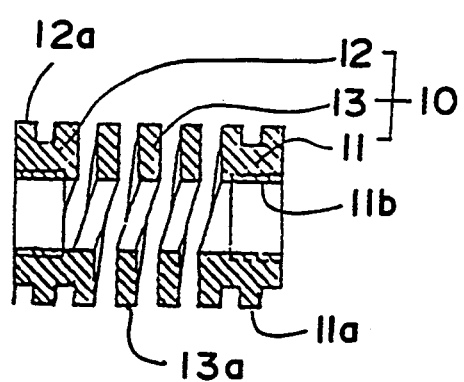
FIG. 1 shows a cross-sectional view of the present invention.
Figure 4:
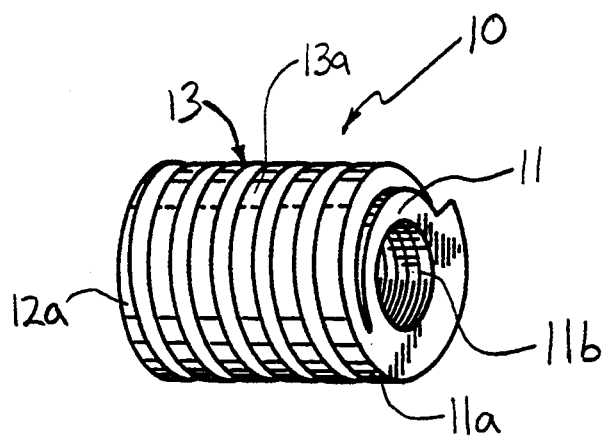
FIG. 4 depicts a perspective view of the interverbral fusing device of the invention.
Figure 5:
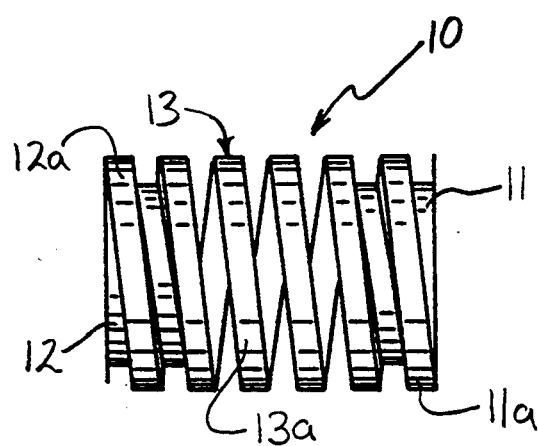
FIG. 5 is a front view of the device of FIG. 4.

Referring to FIGS. 1, 4 and 5, a spiral elastic body 10 embodied in the present invention is shown comprising an integrally formed inward spiral ring mount 12 located at one longitudinal end of the spiral elastic body 10 which is inserted into the vertebra, an integrally formed outward spiral ring mount 11 located at another longitudinal end of the spiral elastic body 10, and a spiralling spring body portion 13.

Figure 2A:
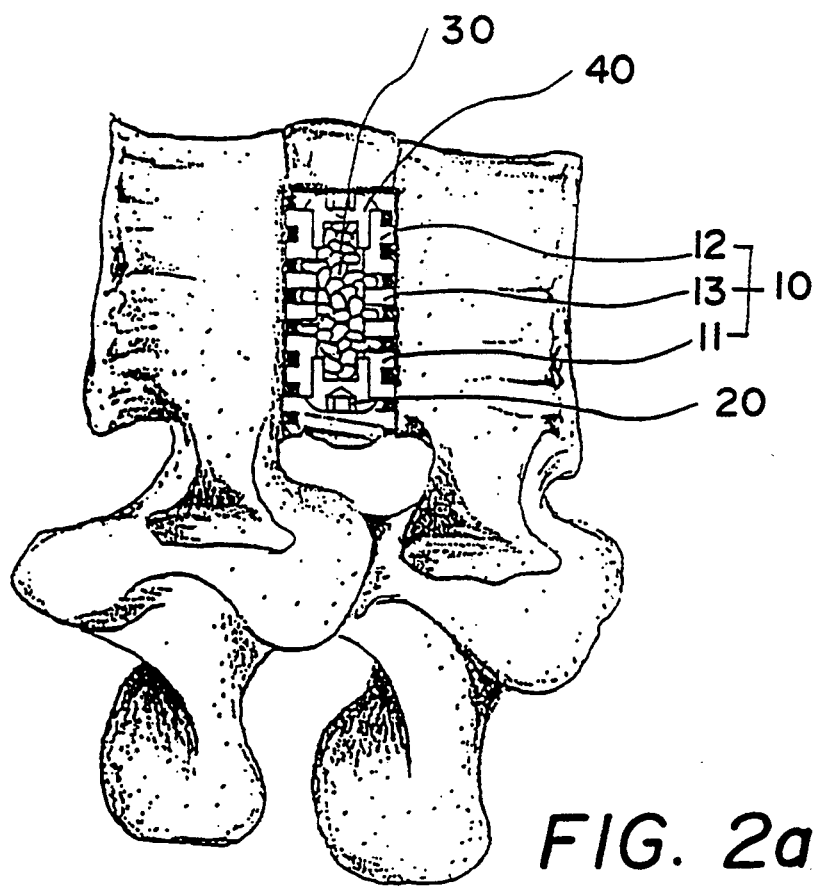
FIG. 2a shows a schematic view of an implanted device of the present invention.
Figure 2B:
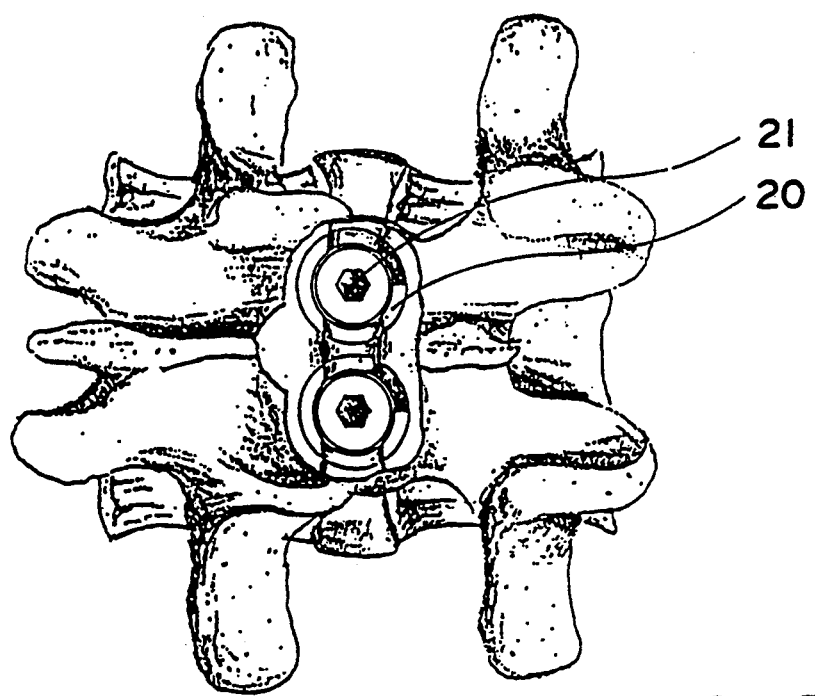

The implanted spiral elastic body 10, as shown in FIGS. 1, 4 and 5 is illustrated in FIGS. 2a and 2b. The sectional view of the implanted spiral elastic body 10 is shown in FIG. 2a, in which the spiral elastic body is shown to comprise a spiral head member 20, bone grafts 30, and an inner mount cover 40. The external view of the implanted spiral elastic body 10, as shown in FIG. 2a, is shown in FIG. 2b in which the spiral head member 20 is shown to comprise a spiral head hole 21. The surgical implantation of the spiral elastic body 10 of the present invention, as shown in FIGS. 2a and 2b, is intended for use in fusing any deformed vertebra of cervical vertebrae, thoracic vertebrae, lumbar vertebrae and sacral vertebrae of a human spinal column.

Figure 3A:
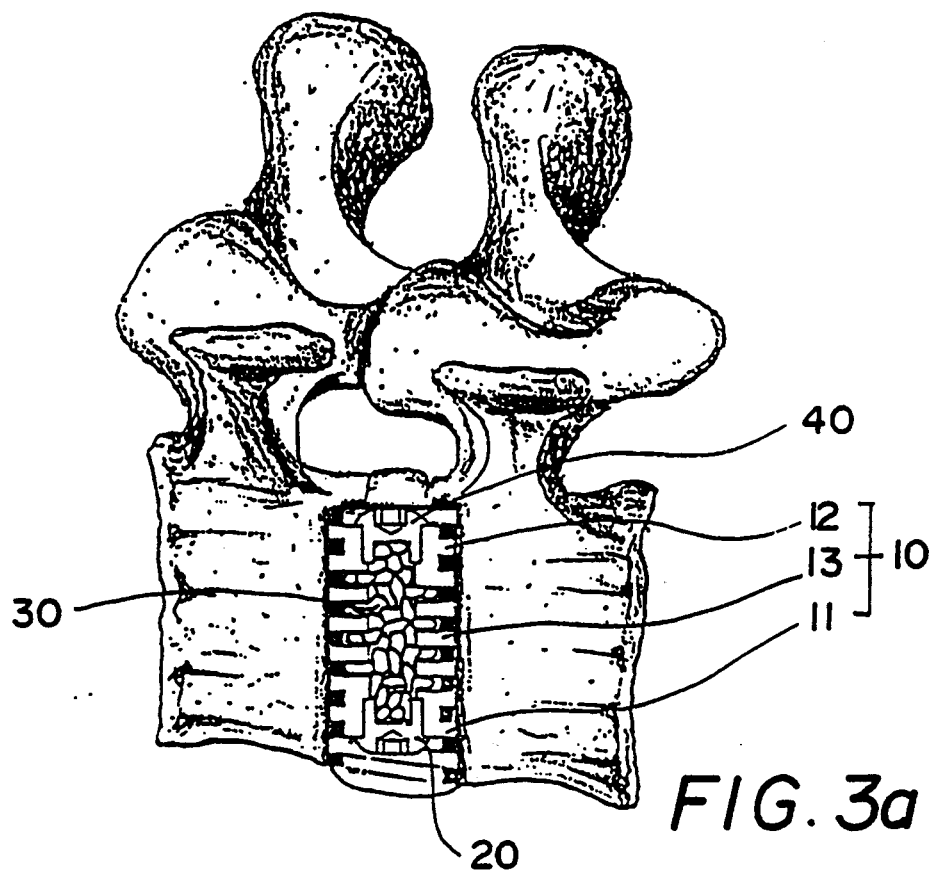
FIG. 3a shows a schematic view of another implanted device of the present invention.
Figure 3B:
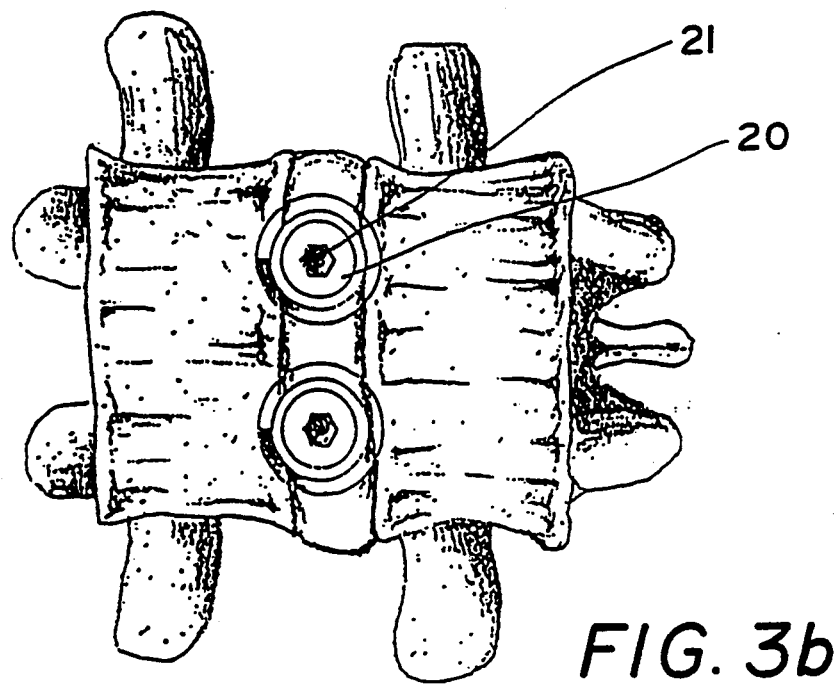

Another surgical method of implanting the spiral elastic body 10 of the present invention, as shown in FIGS. 3a and 3b, is intended for use in fusing any deformed vertebra of the coccygeal vertebrae and the sacral vertebra adjacent to the coccygeal vertebrae.

The spiral elastic body 10 is designed to have an associated elasticity approximately corresponding to that of the vertebrae. However, the spring body portion 13 of the spiral elastic body 10 may be so constructed as to have varying elastic properties, depending on the surgical requirements. The spring body portion 13 13a is adapted to be inserted into the two vertebrae by threading each of the spiral loops 13a into the vertebrae.

The spiral elastic body 10 of the present invention is made of an elastic material biocompatible with the human vertebrae and suitable for use in the orthopedic surgery. The recommended materials include the stainless steel 316 LVM, the Ti-6-4 material, the cobalt-molybdenum-nickel alloy, etc.

The spiral elastic body 10 of the present invention may be made up of a simple spring body having a first or outward end provided with a spiral ring mount. In addition to the outward spiral ring mount, the simple spring body should preferably have a second or inward spiral ring mount located at an inward end thereof. The term "inward end" used above refers to the end of the spiral elastic body 10 that is inserted into the vertebra, while the term "outward end" used above refers to another end opposite to the inward end.

The spiral ring mounts 11 and 12 of the spiral elastic body 10 are provided respectively on the outer surface thereof with spirally projectors 11a and 12a respectively made integrally therewith. As a clearly shown in FIGS. 1, 2a, 3a and 5, each spiral ring mount 11, 12 constitutes a thickened section of elastic body 10 with each spiral ring mount having an associated longitudinal thickness which is greater than the longitudinal thickness of any given loop 13a and actually greater than two consecutive loops 13a. The spiralling projections 11a and 12a, of the spiral ring mounts 11 and 12 are similar in screw pitch and shape to the spiral loops 13a of the spiral elastic body 10. In essence, spiralling projections 11a and 12a and spiral loops 13a together can constitute a single external thread which allows complete threading of the entire spiral elastic body 10 into vertebrae. The outward spiral ring mount 11 is united with the spiral head member 20 by any known fastening means. In other words, the outward spiral ring mount 11 is provided on the inner surface thereof with threads 11b engageable with threads of the spiral head member 20.

The spiral head member has an outward end provided with a head of octagonal construction and having a cruciform groove or a horizontal straight groove. The spiral head member has an inward end that is united with the outward end of the spiral elastic body by any known fastening means.

The bone grafts used in the embodiment of the present invention are synthetic bone grafts, such as those made by Kyocera Corp. of Corp. of Japan under the trademark BIOCERAM, which are affinitive to the cells and the tissues of the vertebrae. In addition to the synthetic bone grafts described above, the natural bone grafts may be used in place of the synthetic bone grafts. The natural bone grafts are grafted from the vertebrae. The bone grafts of appropriate size and shape are housed in a chamber formed by the spiral elastic body and the spiral head member. If a block of synthetic bone grafts is used as a bone healing material in the surgical implantation of the device of the present invention, the outward end of the synthetic block may be used to act as a spiral head in lieu of the spiral head member. In other words, the synthetic block and the spiral head member are made integrally so as to fit into the spiral elastic body. Like natural bone grafts, the synthetic bone healing body may be of fragmentary form. The spiral elastic body is implanted in such a manner that the inward end of the spiral elastic body urges the bottom of the vertebra. As a result, the inward end of the spiral elastic body may be devoid of an inward end mount cover. In order to prevent the inward end of the spiral elastic body from not biasing the bottom end, an inward mount cover may be fastened to the spiral elastic body before the surgical implantation. The inward mount cover may be made separately and then attached to the spiral elastic body or made integrally with the spiral elastic body. The inward mount cover is attached to the spiral elastic body by any known fastening means.

The surgical procedures of implanting the device of the present invention are similar to the conventional surgical procedures. Generally speaking, it is suggested that the spiral elastic body of the present invention is preferably provided with an inward spiral ring mount and an outward spiral ring mount. The device of the present invention is used in pairs, thereby forming four supporting points by two inward spiral ring mounts and two outward spiral ring mounts. These four supporting points are not necessarily on the same plane. However, the four supporting points tend to remain on the same plane so as to unite completely and intimately with the vertebrae in view of the fact that spiral ring mounts are fastened to the elastic body. As a result, the device of the present invention can be fused completely and intimately with the vertebrae. Upon the completion of the surgical implantation, the linguiform formation of new bone is brought about to effect the healing process. In addition, the effect of the micromotion taking place between the implanted device of the present invention and the vertebrae is helpful to the recovery of the deformed vertebra at a pace, which is faster than that of the prior art device.

The embodiment of the present invention described above is to be regarded in all respects as merely illustrated and not restrictive. Accordingly, the present invention may be embodied in other specific forms without deviating from the spirit thereof. The present invention is therefore to be limited only by the scope of the following appended claims.

I claim:

1. An intervertebral fusing device comprising a spiral elastic body having first and second longitudinally spaced ends interconnected by a spring body portion, the first end of said spiral elastic body being defined by a first spiral ring mount having an outer surface provided with a spiralling projection, the second end of said spiral elastic body being defined by a second spiral ring mount having an outer surface provided with another spiralling projection, said spring body portion being defined by a plurality of spiral loops, the first and second spiral ring mounts and the spiral elastic body being integrally formed with the spiralling projections provided on the respective outer surfaces of said first and second spiral ring mounts and the plurality of spiral loops of said spiral elastic body constituting a single thread having a constant pitch and shape from the first end of the spiral elastic body to the second end thereof for threadably securing said intervertebral fusing device to a vertebra, each of said first and second spiral ring mounts having an associated longitudinal thickness that is greater than a longitudinal thickness of any one of the plurality of spiral loops of said spring body portion.

2. The intervertebral fusing device of claim 1, wherein both of said first and second spiral ring mounts include internally threaded portions, said intervertebral fusing device further comprising a mount cover and a head member, said mount cover being threadably attached to the internally threaded portion of said second spiral ring mount and said head member being threadably attached to the internally threaded portion of said first spiral ring mount.

3. The intervertebral fusing device of claim 2, wherein said spiral elastic body and said head member form an unsealed chamber adapted to receive one or more bone grafts, affinitive to cells and tissues of a vertebra to which said intervertebral fusing device is adapted to be attached.

* * * * *